US007232220B2

(12) United States Patent
Franz et al.

(10) Patent No.: US 7,232,220 B2
(45) Date of Patent: Jun. 19, 2007

(54) SYSTEM FOR VISION EXAMINATION UTILIZING TELEMEDICINE

(76) Inventors: Richard Franz, 5259 Hiddencrest Ct., Concord, CA (US) 94521; John Weber, 8119 Regency Dr., Pleasanton, CA (US) 94588

( * ) Notice: Subject to any disclaimer, the term of this patent is extended or adjusted under 35 U.S.C. 154(b) by 119 days.

(21) Appl. No.: 10/087,697

(22) Filed: Mar. 1, 2002

(65) Prior Publication Data
US 2003/0117580 A1 Jun. 26, 2003

Related U.S. Application Data

(60) Provisional application No. 60/272,054, filed on Mar. 1, 2001.

(51) Int. Cl.
*A61B 3/10* (2006.01)
(52) U.S. Cl. ...................................... 351/205; 351/246
(58) Field of Classification Search ................ 351/205, 351/222, 246, 206; 705/2, 3; 707/10, 104.1; 600/300–595; 128/904, 905, 906, 920, 922
See application file for complete search history.

(56) References Cited

U.S. PATENT DOCUMENTS

| | | | |
|---|---|---|---|
| 4,761,071 A | 8/1988 | Baron | |
| 5,617,157 A | 4/1997 | Shalon et al. | |
| 5,694,199 A | 12/1997 | Rodriguez | |
| 5,895,371 A * | 4/1999 | Levitas et al. ............. | 604/500 |
| 5,897,493 A * | 4/1999 | Brown ....................... | 600/300 |
| 5,903,889 A * | 5/1999 | de la Huerga et al. ........ | 707/3 |
| 5,912,720 A | 6/1999 | Berger et al. | |
| 5,914,772 A | 6/1999 | Dyer | |
| 5,926,247 A * | 7/1999 | Kimura ..................... | 351/178 |
| 5,943,116 A | 8/1999 | Zeimer | |
| 5,956,121 A * | 9/1999 | Hosoi et al. ................ | 351/205 |
| 5,993,001 A * | 11/1999 | Bursell et al. .............. | 351/212 |
| 6,003,991 A | 12/1999 | Viirre | |
| 6,022,315 A | 2/2000 | Iliff | |
| 6,027,217 A * | 2/2000 | McClure et al. ............. | 351/246 |
| 6,033,076 A | 3/2000 | Braeuning et al. | |
| 6,080,106 A * | 6/2000 | Lloyd et al. ................ | 600/300 |
| 6,106,463 A * | 8/2000 | Wilk .......................... | 600/437 |
| 6,112,224 A * | 8/2000 | Peifer et al. ................ | 709/202 |
| 6,238,049 B1 * | 5/2001 | Griffin et al. ............... | 351/243 |
| 6,386,707 B1 * | 5/2002 | Pellicano .................... | 351/246 |
| 6,409,661 B1 * | 6/2002 | Murphy ...................... | 600/300 |
| 6,523,954 B1 * | 2/2003 | Kennedy et al. ............ | 351/205 |
| 6,820,057 B1 * | 11/2004 | Loch et al. .................. | 705/2 |
| 2001/0032100 A1 * | 10/2001 | Mahmud et al. ............ | 705/2 |

* cited by examiner

*Primary Examiner*—Hung Xuan Dang
(74) *Attorney, Agent, or Firm*—Stout, Uxa, Buyan & Mullins, LLP; Frank J. Uxa; Carlos A. Fisher

(57) ABSTRACT

The telemedicine method and system disclosed includes at least one remote exam module which in turn includes a plurality of optical devices configured to examine a patient's eye, and a controller for collecting and transmitting the examination data of the patient's eye. The information collected is transmitted via a communications link to a diagnostic center for analyzing the information collected at the remote exam module. The diagnostic center further maintains a database of patient records corresponding to the remotely collected examination information and an exam console for enabling a diagnosis based on the collected information.

18 Claims, 2 Drawing Sheets

SYSTEM FOR VISION EXAMINATION UTILIZING TELEMEDICINE

BACKGROUND OF THE INVENTION

This application claims priority from Provisional Application Ser. No. 60/272,054, filed on Mar. 1, 2001.

FIELD OF THE INVENTION

The present invention relates to systems and methods for examining a patient's vision, and more particularly, to imaging systems and communications systems that enable the ophthalmic diagnosis of a patient in a remote location.

DESCRIPTION OF THE PRIOR ART

A number of systems have been developed for use in medical examinations, some of which can be applied in a telemedicine context, i.e., in which data or results from the examination are transmitted over an electronic or other communication link and saved in a central electronic medical record database so that a physician or other medical worker need not be in the same location as the patient. For example, telemedicine systems for performing vision testing and eye examination are described in U.S. Pat. Nos. 4,761,071; 5,617,157; 5,694,199; 5,912,720; 5,943,116; 5,993,001; 6,003,991; 6,022,315; 6,027,217; and 6,033,076. Those patents, however, only use either a camera or a video/audio feedback mechanism as diagnostic equipment. Thus, the patents do not disclose systems or methods for collecting a patient's tonometry, blood pressure, anterior segment evaluation, corneal topography, refraction, etc., such as to enable a full examination of the eye.

To avoid increasing the risk of blindness and other eye diseases, individuals should have their vision fully examined at least once a year. Because of illness, location, time constraints or other factors, some individuals cannot readily travel to central medical facilities or other eye care facilities. Accordingly, there is a need in the art for a system that integrates the operation of several optical devices to allow a vision examination to be conducted on a patient from a remote location.

SUMMARY AND OBJECTS OF THE INVENTION

The present invention provides a unique telemedicine method and system including at least one remote exam module which in turn includes several optical devices configured to examine a patient's eye, and a controller for collecting information from the plurality of optical devices, as well as for controlling the examination of the patient's eye.

The method and system of the invention further includes a diagnostic center for analyzing the information collected and a communications link connecting the diagnostic center to the remote exam module and for transmitting the information collected from the remote exam module to the diagnostic center. The diagnostic center may further include a central electronic database for saving and maintaining records corresponding to the collected information and an exam console for enabling a diagnosis based on the collected information.

It is therefore a primary object of the present invention to provide a method and system for examining the eyes of a patient and to enable the determination of the condition of the eye, as well as the diagnosis of eye disorders and diseases at a location remote from the patient.

It is a further object of the present invention to provide the patient with a diagnostic report and necessary prescriptions before the patient leaves the examination location.

Still further, it is another object of the present invention to achieve the foregoing objectives by enabling the communication of examination data collected by optical devices via a communications link capable of transmitting high-resolution images.

With these and other objects, advantage and features of the invention that may become hereinafter apparent, the nature of the invention may be more clearly understood by reference to the following detailed description of the invention, the claims and to the accompanying drawings.

BRIEF DESCRIPTION OF THE DRAWINGS

The preferred embodiments of this invention will be described in detail, with reference to the following figures, wherein.

DETAILED DESCRIPTION OF THE PREFERRED EMBODIMENTS

Figure 1:
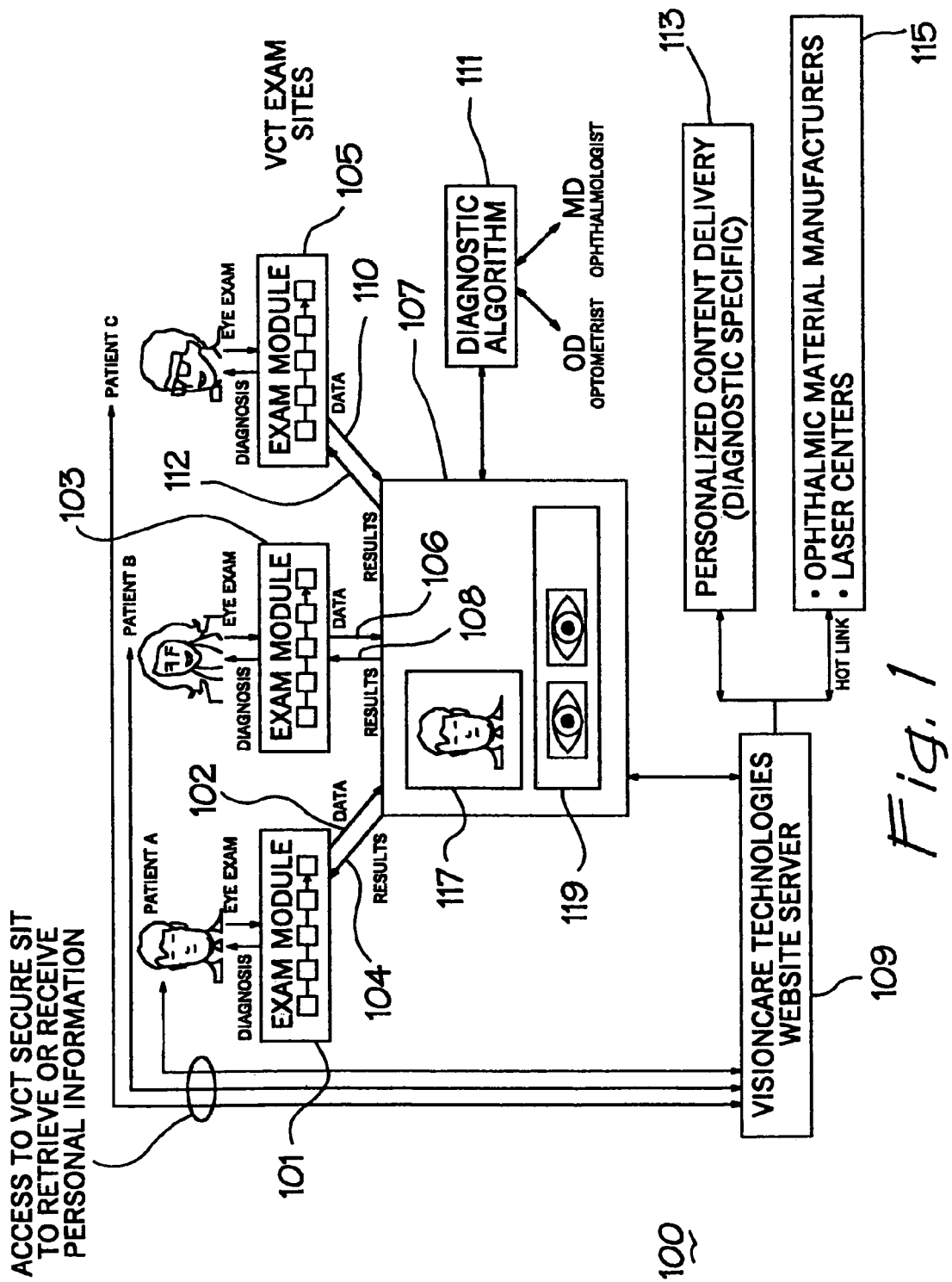
FIG. 1 is a schematic view of one embodiment of the system of the present invention.

The present invention incorporates the use of commercially available ophthalmic diagnostic equipment and software. The equipment is integrated via hardware and software into a comprehensive telemedicine eye examination system. This system is designed to be operated independently by the individual who desires that his or her eyes be examined or with the assistance of a vision care technician. This system is generally comprised of three sub-systems, the examination site, the Internet transmission center and the diagnostic center. The examination site is the location wherein the patient interacts with the system for self testing using the ophthalmic diagnostic equipment, or where the technician administers the testing to the patient, to gather the relevant information. The examination site is generally remote from the diagnostic center, however it can be appreciated that the remoteness of the location may comprise the distance of a room, or may include a distance of many thousands of miles. The Internet transmission center comprises both the hardware and software that permits the examination site and diagnostic center to interface and communicate with each other. The diagnostic center comprises the physical location wherein the optometrist or ophthalmologist reviews the examination data and makes the patient's diagnosis.

The examination software is based upon commercially available ophthalmic diagnostic equipment and software, integrated via commercially available and custom developed hardware and software into a comprehensive eye examination system which can be hosted on a standard PC. This software drives the equipment that captures the eye examination data. The captured data is then transmitted to a central electronic medical record database in a remote diagnostic center where it is saved as part of the examination process. The data for a patient is displayed on an examination console for the supervising eye care practitioner to make the diagnosis. With respect to the present invention, an eye care practitioner includes but is not limited to an ophthalmologist, optometrist, optician or other individual licensed to examine the eye and use of one or another term herein is not meant to be limiting. Once the examination is completed, the patient receives a printed summary report of the examination from the exam module and may receive a printed prescription.

The main features of the present invention include:

Integration of diagnostic equipment and the data captured by the diagnostic equipment for transmission to the diagnostic center and subsequent validation.

Video conferencing system to allow visual interaction between a patient sitting in a remote examination location and an eye care practitioner working from the diagnostic center during an examination.

Display of patient data screens that provide patient information to the remote eye care practitioner.

Creation of a patient data report, which includes a summary report of the patient's vision testing, a printed copy of which is delivered to the patient upon completion of the examination.

Referring now to the schematic drawings, FIG. 1 shows a high-level block diagram of the system 100 of the present invention. The system 100 includes a plurality of exam modules 101, 103, and 105; a diagnostic center 107; a medical record database 209 (see FIG. 2); and a computer 111 for executing a diagnosis algorithm. The medical record database 209 as well as the computer 111 is preferably located in the diagnostic center 107. The system 100 may also include a server 109 hosting a web site.

Figure 2:
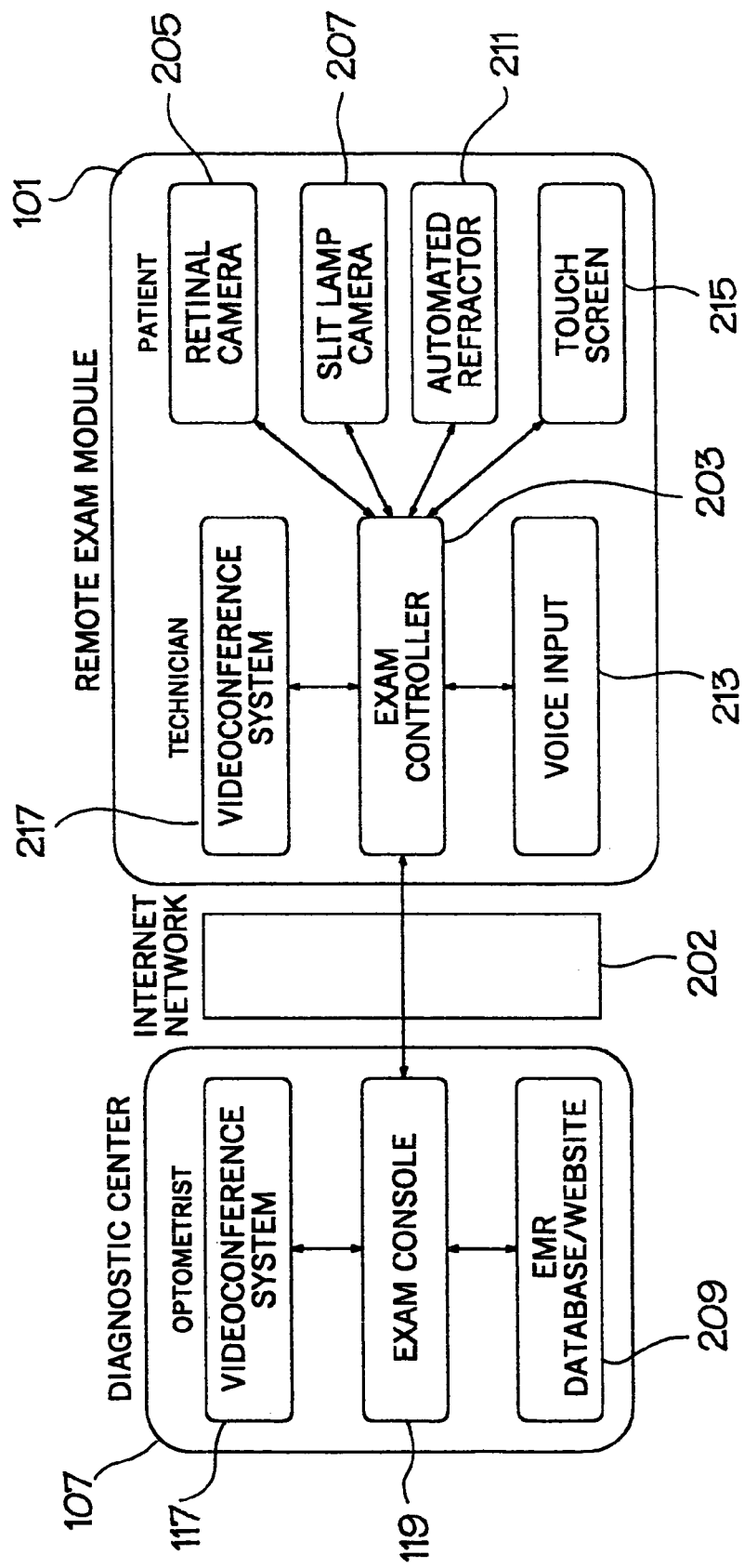
FIG. 2 is a schematic view of one embodiment of an exam module and a diagnostic center of the present invention.

With reference to FIG. 2, the diagnostic center 107 includes an exam console 119 and a video conferencing system 117. The exam modules 101, 103, and 105 are identical in function and structure so that only one will be described herein. FIG. 2 illustrates the exam module 101, which is also used as an example in the description that follows. Typical diagnostic equipment includes that which is used in normal and customary eye examinations and may include any one or more of, but is not limited to, the following: lensometer, tonometer, visual fields tester, fundus camera, retinal imaging systems, posterior segment imaging systems, automated refractor, biomicroscope and/or corneal topographer.

Exam module 101 is at a location (e.g., an office, room, etc.) where a patient sits to be examined. The term remote location as used herein can be any location whereat the patient and the diagnosing eye care practitioner are in different locations, including being in different rooms, buildings, cities or other separation in space. At this location, which is remote from the diagnostic center 107, the patient's vision is tested and the test data is collected and sent to the diagnostic center 107 via a link 102, for example. As shown in FIG. 1, the data links 102, 106, and 110 correspond to the exam modules 101, 103, and 105, respectively.

The teleconference system 117 may use a communications link supporting the transmission of low-resolution images in real-time, for example in M-PEG format. The teleconference system 117 is optionally used for the real-time communication between an eye care practitioner located at the diagnostic center 107, and either a patient undergoing examination or a technician assisting in the examination, both of whom would be physically present at one of the exam modules 101, 103, 105.

The exam console 119 in the diagnostic center includes a standard personal computer ("PC") able to process high-resolution images transmitted from the exam module 101 (e.g., pictures of the eye) which are displayed to the eye care practitioner. The high-resolution images correspond to the examination data captured by ophthalmic diagnostic equipment in the exam module 101, such as a retinal camera 205, a slit lamp camera 207, and an automated refractor 211 as shown in FIG. 2. The exam console is preferably comprised of a series of computer monitors set up to present the data provided to the exam console by the exam controller using commercially available hardware links between the various pieces of equipment as well as the video conferencing system. In practice, the exam console interacts with the electronic medical records database and the system software to assimilate the data for presentation to the technician, the eye care practitioner or the patient. The exam console may also present to the optometrist or ophthalmologist, care and treatment suggestions from the database and textbook entries, thus assisting the optometrist or ophthalmologist in making the patient's diagnosis as well as providing assistance to the optometrist or ophthalmologist in ways to advise the patient.

The captured data is sent to the diagnostic center 107 via a communications link 102. Thus, in addition to supporting the transmission of low-resolution images to the teleconferencing system 117 to enhance the interpersonal aspects of the system, the data communications link 102 supports the transmission of high-resolution images to the exam console 119. The standard for transmission of data corresponding to the high-resolution images may be dictated by the optical device (e.g., retinal camera 205 in FIG. 2) which initially captures the data. The communications link 102 provides sufficient bandwidth to transmit the data in real-time, regardless of the data transmission protocol.

The database electronically stores all of the patient information for access by the patient, technician or practitioner, as appropriate, at any time via the vision care website. The database is also designed to enable collection of data from multiple patients, creation of statistics using the data contained therein and to analyze the data thereby allowing practitioner to search for and research population group trends, changes or expectations based on various criteria. The database 209 is preferably hosted on a high bandwidth server that maintains all optical records. The database may utilize commercially available hardware and software. The records database software is designed to interface with the custom system software. The database 209 may also be available for access via a web interface, such as that provided by the web site 109. In practice, the exam console input is stored in the records database. Data may be included or added to the records database by the system software based on a variety of factors. Patient records may be stored and accessed from the database by the exam console or diagnostic center and can be accessed by the technician or practitioner using the exam controller, the exam console or vision care website, as appropriate. Patients can access the web site 109 to view their private examination data or prescriptions that may be stored in the database 209 once they have been granted access (e.g., by a password) by a database administrator. Other health professionals may also view the examination data on the web site so long as they are provided with proper access to the database 209. Data encryption technology may be utilized to ensure the safety of patient records.

The computer 111 may run, for example, software that performs advanced statistical analysis on the collected examination data and software that detects pathological conditions and advises the supervising eye care practitioner of any important issues. For example, if the patient has elevated intraocular pressures, a marginal cup/disc ratio and visual field anomalies, an algorithm will indicate the probability of the patient having glaucoma. In another example, if the patient is a middle aged person with variable vision and exhibits retinal cotton-wool exudates, an algorithm will indicate the probability of that person having diabetes.

The eye care practitioner may then use the teleconference system 117 to resolve the issues with the technician assisting in the examination at the exam module location 101. The eye care practitioner may then review the collected data as well as the results of the analysis to determine the diagnosis and treatment and to complete an examination report. The examination report is then transmitted to the examination module 101 via the communications link 104, where it can be printed for the patient's personal records. The links 108 and 112 perform the same functions as link 104 but with respect to exam modules 103 and 105.

The exam module 101 may include special fixtures to allow the patient to sit in a single location and enable individual pieces of equipment to be quickly and easily moved into and out of position at the patient's location. This increases the patient's comfort level as well as decreases examination time.

In addition to the cameras 205, 207, and refractor 211, the exam module 101 may include other optical diagnostic equipment, such as a case history capture device, a lensometer, a tonometer, a visual fields tester, a fundus camera, a biomicroscope, and a corneal topographer.

All of the foregoing optical diagnostic equipment are well known in the field of eye vision examination. In essence, the information that may be collected by such devices includes fundus information, refraction information, the patient's visual acuity, neutralization of the habitual prescription, tonometry information, visual fields information, blood pressure information, anterior segment information, corneal topography information, and intraocular lens status. These devices may offer RS-232 serial port, parallel printer port, USB port remote connectivity or other standard connection device. The above ports can be used to remotely control these devices, and results for diagnosis can be acquired via the ports.

The exam controller 203 may be a commercially available PC, preferably running an embedded operating system, for example, embedded Windows NT. It may include external connections to simultaneously control all of the optical diagnostic equipment in the exam module 101 as well as external interfaces such as voice input capabilities and touch screen input to allow the patient or technician to enter the relevant information into the system. The exam controller 203 controls the examination process by sequentially controlling the operation of each piece of diagnostic equipment and collecting examination information from the diagnostic equipment. The software may be proprietary for example, and is programmed to manage the equipment interface, data flow as well as the transport of high-resolution images and low-bandwidth video images. The exam controller 203 provides the patient with the examination results via the computer monitor.

In practice the patient or technician using the exam controller 203 will enter the requisite information into the exam controller 203 by any conventional method, including for example, personal computer keyboard, voice input system 213 or touch screen 215. The patient may enter information for either creating or updating a record by answering a displayed questionnaire. Once the information has been entered the software manages the exam sequence in such a way so as to take into account patient reaction, reactions by the technician if appropriate, diagnostic equipment interface, technical data entered to the system, relevant patient information, the type of exam being conducted, and any information entered into the exam console or at the diagnostic center if appropriate. The exam controller includes separate interface modules which may combine to act in concert when appropriate. These interface modules allow the exam controller 203 to communicate with the various pieces of equipment in a manner consistent with the protocol used by each such piece of equipment. When in use the exam controller 203 will indicate to the technician, patient or diagnostic equipment, as appropriate, that the specific task is ready to commence. In response, the technician, patient or equipment, as appropriate will signal the equipment to proceed. Once the test has been run or the equipment has completed its performance, the exam controller will use its interface module to collect and receive the data and transmit such to the exam console in the diagnostic center for review by the ophthalmologist or optometrist. Both the exam controller and the exam console are capable of managing and controlling the transmission of information between the two systems. The exam controller may also enable video conferencing between the patient and/or technician and the optometrist or ophthalmologist located at the diagnostic center location.

It may be appreciated that biometrics may be utilized for exam initiation to ensure the patient ID and record match the patient. The exam controller 203 either creates or locates the patient record and creates an examination record in the database 209. The data may be sent to the database 209 via communications link 102 (FIG. 1). The links 104 and 102 may be implemented as an Internet connection or remote link 202 (FIG. 2).

The exam controller 203 may also support a low-resolution video-conference camera incorporated in the teleconference system 217.

When an exam is started, the examination data for that patient is brought up on the console. As the technician (or the patient) administers the data collection, the data is transferred to the exam console 107 and the eye care professional reviews the data and creates a report. After the report is created, it is transmitted to the exam controller 203 where the results are printed out for the patient.

The remote link or Internet connection 202 facilitates two-way communication between the exam controller and the exam console in the diagnostic center. The hardware utilized to create the remote link is commercially available and includes, router, hubs, ports and other similar equipment typically found in an electronic communication center. The remote link may also be capable of utilizing commercially available data, as well as voice and/or video communication software. In practice, the preferred connection for the remote link is one having a high-bandwidth, however, dial-up connection or a wireless connection may be used, however, for video conferencing a minimum of ISDL is recommended.

Encryption and decryption of all patient data ensures that the operators of the system 100 maintains control and confidentiality in all aspects of patient care and communication. The encryption may be applied to data before transmission through any of the communication links or before storage in the database 209.

The system 100 utilizes several software components. For example, the exam controller software is a piece of software hosted by embedded Windows NT. This software may include interface modules, which allow it to communicate with the many variations of ophthalmic diagnostic equipment on the market. Each piece of equipment may have its own private protocol, which must be observed. This software ensures compatibility with the major vendors of optical diagnostic equipment. The exam controller software may include a core component to manage the flow of data from the exam process performed in an examination module to the database 209 and the exam console 107. The data may include textual data, high-resolution images and low bandwidth video-conferencing transmissions. The exam controller 203 may include a local interface that is used by the technician to execute the examination.

The database 209 may be a commercially available database running on a commercially available 24/7-uptime server. This server is preferably backed up and may be redundant.

The web site 109 provides a web front end to the database 209 and a corporate web presence. The website permits patients to access their own personal records via an Internet connection, including access to their vision wear prescription and the ability to transmit their personal information to a qualified eye care professional for purchase of prescription eye wear. The patient may also utilize the website to provide other eye care professionals with access to his or her own medical records and eye exam/care history. The website may also serve as an information center which includes links to other informational websites and ocular business sites. The website will utilize standard input and functionality screens and can be accessed in the normal course of Internet and World Wide Web browsing. Software utilized in the operation of a web site is well known in the art and therefore need not be described in detail herein.

The exam console software may be a custom piece hosted by Windows NT/2000 or EP. This software is designed to manage all interface between the various commercially available hardware and software contained in this vision care system including each of the hardware and software platforms. This software must be designed to integrate the diagnostic equipment and the data transmission to a remote site as well as validate the data transmitted in such transmission, manage video conferencing, develop a central diagnostic center for practitioners to evaluate the patient's data, design patient data screens to provide information to the remote practitioner, develop a patient report, manage and conduct the remote eye exam. This software may graphically display the components of the eye examination, manage video-conferencing, and handle submission of the examination data to the database 209 and the exam controller 203.

While this invention has been described in conjunction with the specific embodiments outlined above, it is evident that many alternatives, modifications and variations are apparent to those skilled in the art. Accordingly, the preferred embodiments of the invention as set forth above are intended to be illustrative and not limiting. Various changes may be made without departing from the spirit and scope of the invention.

What is claimed is:

1. A method of conducting a comprehensive eye examination from a remote location, comprising
examining an eye of a patient at an eye examination location using a plurality of eye examination devices at the eye examination location to provide eye examination data;
transmitting the eye examination data to a diagnostic center remotely located from the eye examination location to enable the diagnosis of an eye disorder or disease of the patient by a licensed eye care practitioner located at the diagnostic center, the diagnostic center including no eye examination devices; and
providing a diagnosis and a prescription, based on the eye examination data, to the patient via a communications link before the patient leaves the eye examination location.

2. The method of claim 1, further comprising:
displaying images corresponding to the transmitted eye examination data; and
diagnosing ophthalmic conditions of the patient by examining the images.

3. The method of claim 2, wherein displaying the images comprises displaying the images in substantially real-time.

4. The method of claim 1, wherein the diagnosis is obtained by analyzing the transmitted eye examination data.

5. The method of claim 4, wherein the analyzing is performed using at least one computer.

6. The method of claim 1, wherein the diagnostic center comprises a database, and the method further comprises updating the patient's health and visual history information to the database after the patient is tested and the diagnosis is provided.

7. The method of claim 6, further comprising providing access to records in the database via a web interface.

8. The method of claim 1, wherein the diagnosis is provided as a report to the patient.

9. The method of claim 1, further comprising exchanging real-time video using a video conferencing system.

10. The method of claim 1, wherein the eye examination data is transmitted through a world wide web interface.

11. The method of claim 1, wherein the eye examination data comprises at least one type of information selected from the group consisting of information provided by the patient; fundus information; posterior segment information; refraction information; neutralization of the habitual description; tonometry information; visual fields information; blood pressure information; anterior segment information; corneal topography; retinal information; intraocular lens status, and combinations thereof.

12. The method of claim 1, further comprising establishing a substantially real-time interactive communication link between the eye care practitioner located at the diagnostic center and the patient located at the eye examination location.

13. The method of claim 1, wherein the transmitted data comprises information provided by the patient, and objective information obtained from examination of the patient's eye.

14. The method of claim 1, further comprising displaying a questionnaire to the patient for collection of patient history data, the questionnaire being displayed on a display unit.

15. The method of claim 14, wherein the display unit comprises a touch-screen, and the method further comprises receiving information about the patient entered using the touch-screen.

16. The method of claim 15, further comprising receiving verbal responses to the questionnaire using a voice activated input unit.

17. The method of claim 15, further comprising providing access of the patient's case history to the patient located at the eye examination location via an Internet web site.

18. The method of claim 1 in which the eye examination devices comprise at least three devices selected from the group consisting of lensometer, a tonometer, a visual field tester, a fundus camera, a retinal imaging system, a posterior segment imagine system, an automated refractor, a biomicroscope, and a corneal topographer.

* * * * *